(12) United States Patent
Cao et al.

(10) Patent No.: US 11,294,082 B2
(45) Date of Patent: Apr. 5, 2022

(54) X-RAY DETECTOR CAPABLE OF MANAGING CHARGE SHARING AT ITS PERIPHERY

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/036,542

(22) Filed: Sep. 29, 2020

(65) Prior Publication Data
US 2021/0026025 A1     Jan. 28, 2021

Related U.S. Application Data

(63) Continuation of application No. 16/742,776, filed on Jan. 14, 2020, now Pat. No. 10,823,862, which is a continuation of application No. PCT/CN2017/094438, filed on Jul. 26, 2017.

(51) Int. Cl.
| | |
|---|---|
| *G01T 1/29* | (2006.01) |
| *G01T 1/164* | (2006.01) |
| *G01T 1/24* | (2006.01) |
| *A61B 6/03* | (2006.01) |

(52) U.S. Cl.
CPC .......... *G01T 1/2985* (2013.01); *G01T 1/1645* (2013.01); *G01T 1/241* (2013.01); *G01T 1/244* (2013.01); *A61B 6/032* (2013.01)

(58) Field of Classification Search
CPC ..... G01T 1/2985; G01T 1/1645; G01T 1/241; G01T 1/244; G01T 1/36; G01T 1/2928; A61B 6/032
See application file for complete search history.

(56) References Cited

U.S. PATENT DOCUMENTS

| | | | | |
|---|---|---|---|---|
| 8,586,937 | B2* | 11/2013 | Bouhnik | G01T 1/2928 250/370.14 |
| 9,261,609 | B2* | 2/2016 | Shahar | G01T 1/247 |
| 10,823,862 | B2* | 11/2020 | Cao | G01T 1/2928 |
| 2005/0167606 | A1* | 8/2005 | Harrison | G01T 1/241 250/370.13 |

(Continued)

FOREIGN PATENT DOCUMENTS

| | | |
|---|---|---|
| CN | 101163988 A | 4/2008 |
| CN | 101918858 A | 12/2010 |

(Continued)

OTHER PUBLICATIONS

Veale, Matthew C., et al. "Characterization of edgeless CdTe detectors for use in hard X-ray imaging applications." IEEE Transactions on Nuclear Science 59.4 (2012): 1536-1543.

*Primary Examiner* — Marcus H Taningco
(74) *Attorney, Agent, or Firm* — IPro, PLLC; Qian Gu

(57) ABSTRACT

Disclosed herein is a detector, comprising: a plurality of pixels; a first guard ring comprising a plurality of segments, wherein the detector is configured to detect charge carriers collected by the segments; a controller configured to detect charge sharing between at least one pixel of the plurality of pixels and at least one segment of the first guard ring.

15 Claims, 18 Drawing Sheets

(56) References Cited

U.S. PATENT DOCUMENTS

| | | | | |
|---|---|---|---|---|
| 2007/0280409 A1* | 12/2007 | Konno | ............... | G01T 1/249 |
| | | | | 378/19 |
| 2012/0267737 A1* | 10/2012 | Chen | ............ | H01L 27/14683 |
| | | | | 257/429 |
| 2012/0313196 A1* | 12/2012 | Li | ............ | H01L 27/1446 |
| | | | | 257/429 |
| 2018/0321395 A1* | 11/2018 | Steadman Booker | .. | G01T 1/244 |

FOREIGN PATENT DOCUMENTS

| | | | |
|---|---|---|---|
| CN | 102695967 A | 9/2012 | |
| WO | 2013088352 A2 | 6/2013 | |
| WO | 2013088362 A1 | 6/2013 | |
| WO | WO-2016158501 A1 * | 10/2016 | ............ G01T 1/17 |
| WO | WO-2017089363 A1 * | 6/2017 | ............ G01T 1/24 |

\* cited by examiner

X-RAY DETECTOR CAPABLE OF MANAGING CHARGE SHARING AT ITS PERIPHERY

TECHNICAL FIELD

The disclosure herein relates to a detector suitable for X-ray (e.g., X-ray fluorescence), particularly a detector that is capable of detecting and handling charging sharing at the periphery of the detector.

BACKGROUND

X-ray fluorescence (XRF) is the emission of characteristic fluorescent X-rays from a material that has been excited by, for example, exposure to high-energy X-rays or gamma rays. By analyzing the fluorescent X-ray spectrum of a sample, the elements in the sample can be identified because each element has orbitals of characteristic energy. For a given atom, the number of possible relaxations is limited. As shown in FIG. 1A, when an electron on the L orbital relaxes to fill a vacancy on the K orbital (L→K), the fluorescent X-ray is called Kα. The fluorescent X-ray from M→K relaxation is called Kβ. As shown in FIG. 1B, the fluorescent X-ray from M→L relaxation is called Lα, and so on.

The fluorescent X-ray can be analyzed either by sorting the energies of the photons (energy-dispersive analysis) or by separating the wavelengths of the fluorescent X-ray (wavelength-dispersive analysis). The intensity of each characteristic energy peak is directly related to the amount of each element in the sample.

Proportional counters or various types of solid-state detectors (PIN diode, Si(Li), Ge(Li), Silicon Drift Detector SDD) may be used in energy dispersive analysis. These detectors are based on the same principle: an incoming X-ray photon ionizes a large number of detector atoms with the amount of charge carriers produced being proportional to the energy of the incoming X-ray photon. The charge carriers are collected and counted to determine the energy of the incoming X-ray photon and the process repeats itself for the next incoming X-ray photon. After detection of many X-ray photons, a spectrum may be compiled by counting the number of X-ray photons as a function of their energy.

Semiconductor X-ray detectors can directly convert X-ray into electric signals. A semiconductor X-ray detector may include a semiconductor layer that absorbs X-ray in wavelengths of interest. When an X-ray photon is absorbed in the semiconductor layer, multiple charge carriers (e.g., electrons and holes) are generated. As used herein, the term "charge carriers," "charges" and "carriers" are used interchangeably. A semiconductor X-ray detector may have multiple pixels that can independently determine the local intensity of X-ray and X-ray photon energy. The charge carriers generated by an X-ray photon may be swept under an electric field into the pixels. If the charge carriers generated by a single X-ray photon are collected by more than one pixel, or by a guard ring adjacent to the pixel ("charge sharing"), the performance of the semiconductor X-ray detector may be negatively impacted. In applications (e.g., elemental analysis) where X-ray photon energy is determined, charge sharing is especially problematic for accurate photon energy measurement, because the energy of an X-ray photon is determined by the amount of electric charges it generates.

SUMMARY

Disclosed herein is a detector, comprising: a plurality of pixels, wherein the detector is configured to count numbers of X-ray photons that incident on each pixel of the plurality of pixels and whose energies fall in a plurality of bins, within a period of time; a guard ring comprising a plurality of segments, wherein the detector is configured to detect charge carriers collected by the segments; a controller configured to detect charge sharing between at least one pixel of the plurality of pixels and at least one segment of the guard ring.

According to an embodiment, the plurality of pixels of the detector are arranged in an array.

According to an embodiment, the detector is configured to count the numbers of the X-ray photons based on charge carriers generated by the X-ray photons and collected by the each pixel.

According to an embodiment, the guard ring of the detector encompasses the plurality of pixels.

According to an embodiment, the controller is configured to detect charge sharing by determining that a voltage detected from the at least one pixel and a voltage detected from the segment start to change in a same time period.

According to an embodiment, the controller is configured to disregard one photon of the X-ray photons when the controller detects charge sharing between the at least one pixel and the at least one segment.

Disclosed herein is a method comprising: receiving an X-ray photon by a pixel of a detector comprising a plurality of pixels and a guard ring comprising a plurality of segments; detecting charge sharing between the pixel and a segment of the guard ring; with charge sharing detected, disregarding the X-ray photon; with no charge sharing detected and an energy of the X-ray photon falls in one bin of a plurality of bins, counting the X-ray photon into a number of X-ray photons that incident on the pixel and whose energy is in the bin.

According to an embodiment, the method further comprises: for each pixel, determining the number of X-ray photons that incident on the pixel and whose energy is in the bin; and determining a total of the numbers for the plurality of pixels.

Disclosed herein is a system comprising any of the detectors described above and an X-ray source. The system is configured to perform X-ray radiography on human chest, abdomen or human teeth.

Disclosed herein is a system comprising any of the detectors described above. The system is an X-ray telescope, or an X-ray microscopy, or a system configured to perform mammography, industrial defect detection, microradiography, casting inspection, weld inspection, or digital subtraction angiography.

Disclosed herein is a cargo scanning or non-intrusive inspection (NII) system, comprising any of the detectors described above and an X-ray source. The cargo scanning or non-intrusive inspection (NII) system is configured for forming an image based on backscattered X-ray.

Disclosed herein is a cargo scanning or non-intrusive inspection (NII) system, comprising any of the detectors described above and an X-ray source. The cargo scanning or non-intrusive inspection (NII) system is configured to form an image using X-ray transmitted through an object inspected.

Disclosed herein is a full-body scanner system comprising any of the detectors described above and an X-ray source.

Disclosed herein is an X-ray computed tomography (X-ray CT) system comprising any of the detectors described above and an X-ray source.

Disclosed herein is an electron microscope comprising any of the detectors described above, an electron source and an electronic optical system.

DETAILED DESCRIPTION

When an X-ray photon is absorbed in a semiconductor layer of an X-ray detector having a plurality of pixels arranged in an array, multiple charge carriers (e.g., electrons and holes) are generated and may be swept under an electric field towards circuitry for measuring these charge carriers. The carriers drift along the direction of the electric field and then diffuse in all directions. The envelope of carrier trajectories can be roughly a conical shape. If the envelope sits on a boundary between at least one pixel of the array and a segment of a guard ring of the X-ray detector, charge sharing occurs ("charge sharing" herein means charge carriers generated from a single X-ray photon are collected by at least one pixel and another structure such as another pixel or a segment of the guard ring). Charge sharing may cause inaccurate measurement of an X-ray photon energy, because the energy of the X-ray photon is determined by the amount of electric charges it generates.

In one embodiment, when charge sharing occurs between a pixel and a segment of the guard ring, the signal of the pixel may be disregarded.

Figure 1A:
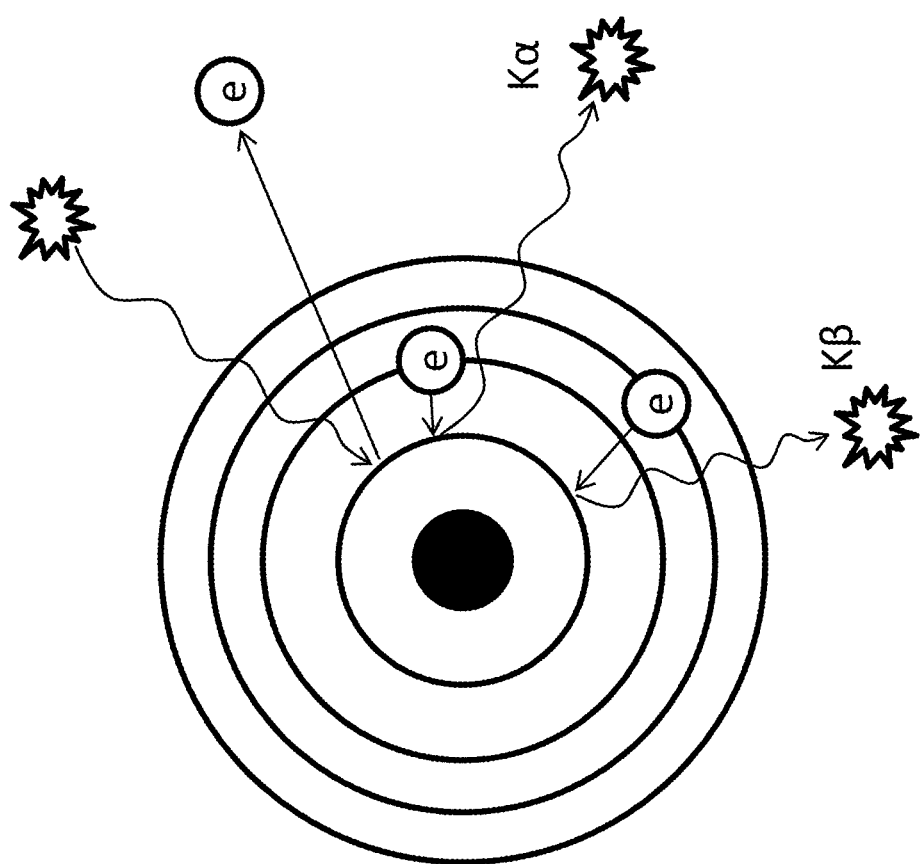
FIG. 1A and FIG. 1B schematically show mechanisms of XRF.
Figure 1B:
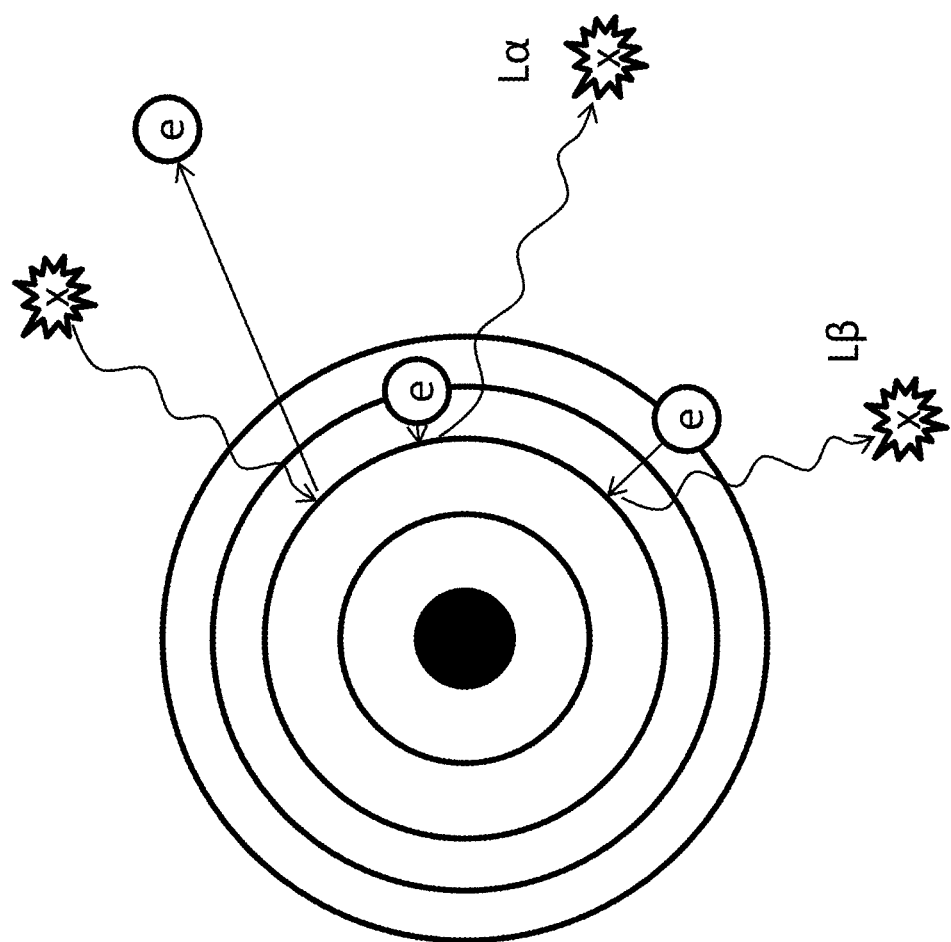
Figure 2A:
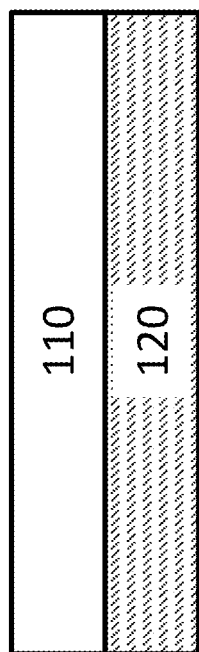
FIG. 2A schematically shows a cross-sectional view of a detector suitable for X-ray, according to an embodiment.

FIG. 2A schematically shows a semiconductor X-ray detector 100, according to an embodiment. The semiconductor X-ray detector 100 may include an X-ray absorption layer 110 and an electronics layer 120 (e.g., an ASIC) for processing or analyzing electrical signals incident X-ray generates in the X-ray absorption layer 110. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 2B:
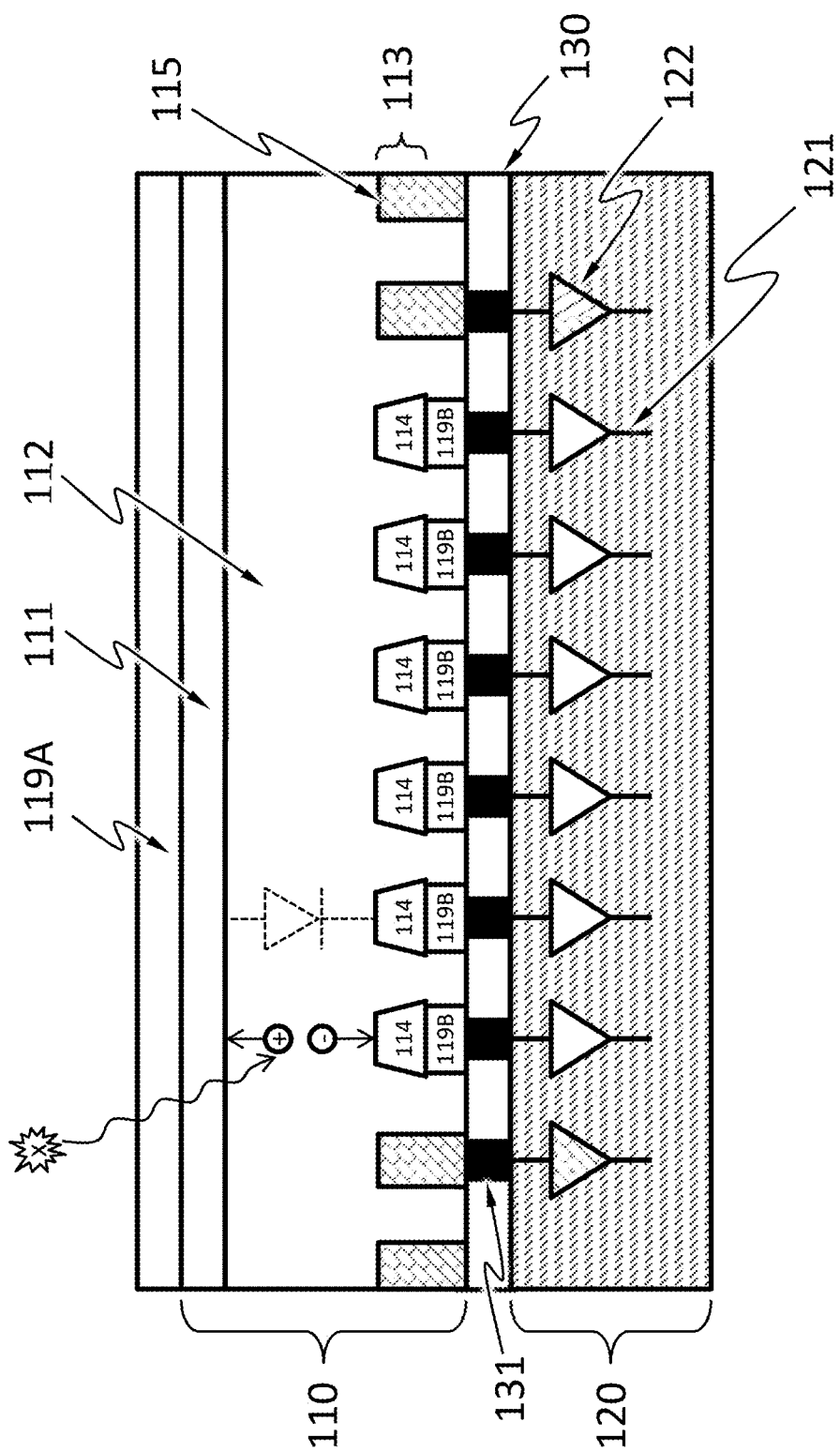
FIG. 2B schematically shows a detailed cross-sectional view of the detector, according to an embodiment.

As shown in a detailed cross-sectional view of the detector 100 in FIG. 2B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 2B, each of the discrete regions 114 of the second doped region 113 forms a diode with the first doped region 111 and the optional intrinsic region 112. Namely, in the example in FIG. 2B, the X-ray absorption layer 110 has a plurality of diodes having the first doped region 111 as a shared electrode. The first doped region 111 may also have discrete portions. In an embodiment, the plurality of diodes in the absorption layer is encompassed by one or several guard rings 115, wherein the guard ring adjacent to discrete regions 114 has discrete segments.

When an X-ray photon hits the X-ray absorption layer 110 including diodes, the X-ray photon may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electric contact 119B may include discrete portions each of which is in electric contact with the discrete regions 114. In an embodiment, the charge carriers generated by a single X-ray photon may be shared by one of the discrete regions 114 and a segment of the guard ring 115.

Figure 2C:
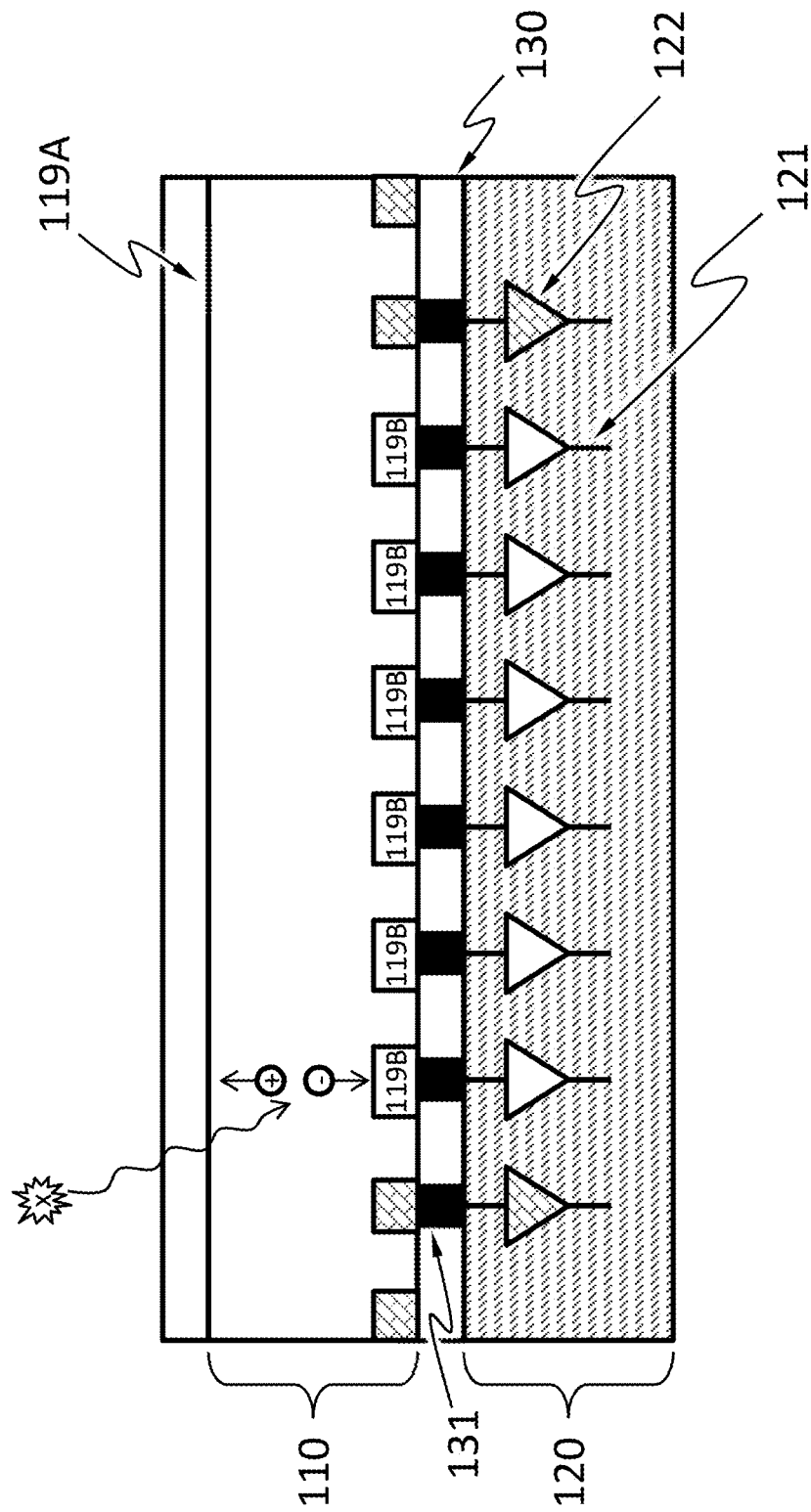
FIG. 2C schematically shows an alternative detailed cross-sectional view of the detector, according to an embodiment.

As shown in an alternative detailed cross-sectional view of the detector 100 in FIG. 2C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electric contacts 119A and 119B under an electric field. The field may be an external electric field. The electric contact 119B includes discrete portions. In an embodiment, the charge carriers generated by a single X-ray photon may be shared by one of the discrete portions of the electric contact 119B and a segment of the guard ring 115.

The electronics layer 120 may include an electronic system 121 and an electronic system 122, suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

The electronic system 122 may include an analog circuitry such as a filter network, amplifiers, integrators, and comparators, or a digital circuitry such as a microprocessor, and memory. The electronic system 122 may include components shared by the segments or components dedicated to a single segment of the guard ring. For example, the electronic system 122 may include an amplifier dedicated to each segment and a microprocessor shared among all the segments. The electronic system 122 may be electrically connected to the segments of the guard ring by vias 131. Space among the vias may be filled with a filler material 130, which may increase the mechanical stability of the connection of the electronics layer 120 to the X-ray absorption layer 110. Other bonding techniques are possible to connect the electronic system 122 to the pixels without using vias.

Figure 3A:
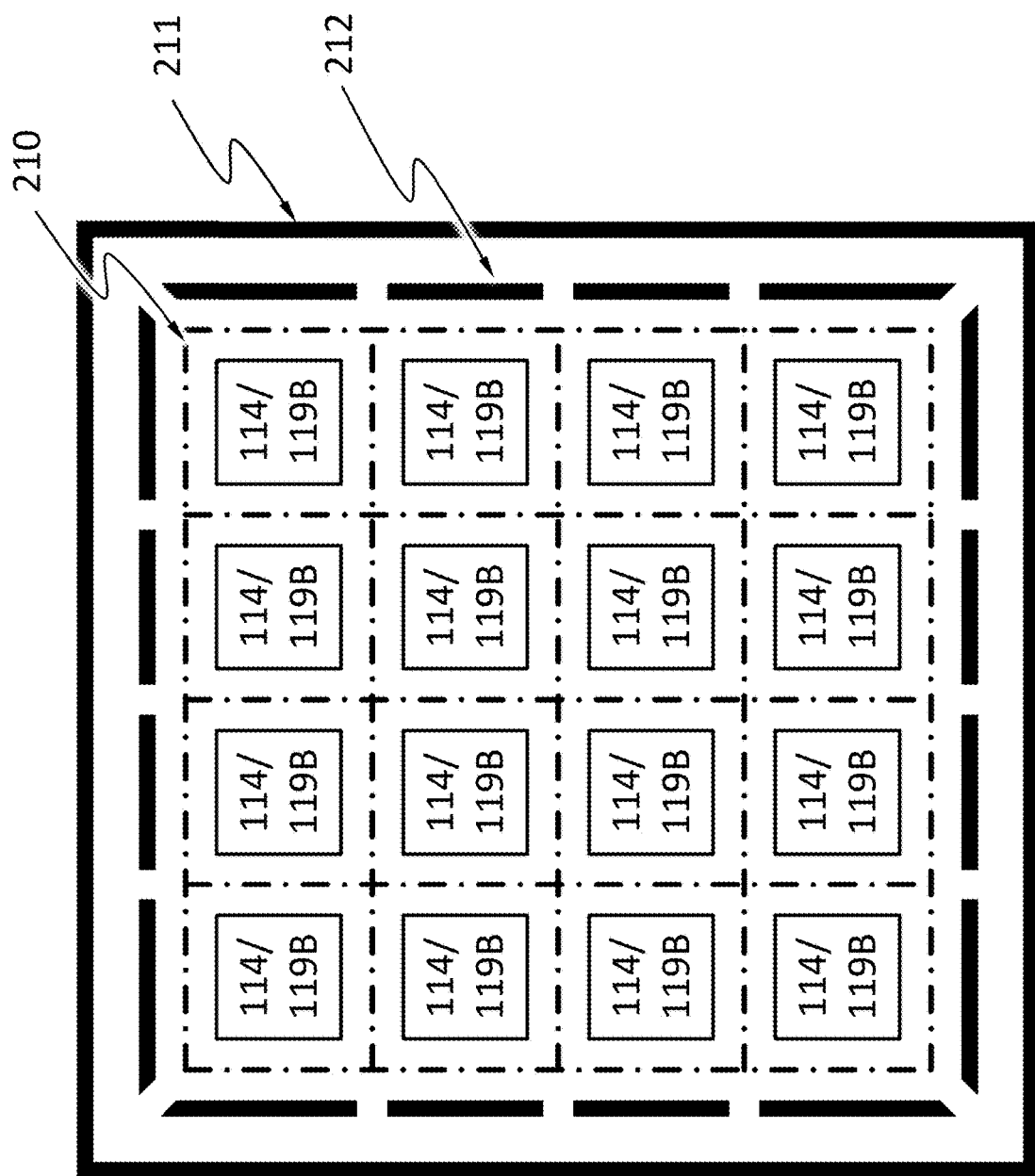
FIG. 3A schematically shows a top view of a portion of the detector, according to an embodiment.

FIG. 3A shows an exemplary top view of a portion of the device 100 with an array of discrete regions 114. Charge carriers generated by an X-ray photon incident around the footprint of one of these discrete regions 114 are not substantially shared with the segment of the guard ring. The area 210 around a discrete region 114 in which substantially all (more than 95%, more than 98% or more than 99% of) charge carriers generated by an X-ray photon incident therein flow to the discrete region 114 is called a pixel associated with that discrete region 114. Namely, less than 5%, less than 2% or less than 1% of these charge carriers flow beyond the pixel, when the X-ray photon hits inside the pixel. The pixels may be organized in any suitable array, such as, a square array, a triangular array and a honeycomb array. The pixels may have any suitable shape, such as, circular, triangular, square, rectangular, and hexangular. The pixels may be individually addressable, and the pixel array may be encompassed by one or several guard rings (such as guard rings 211 and 212). The guard ring 212 may have discrete segments.

Similarly, when the array in FIG. 3A indicates an array of discrete portions of the electric contact 119B in FIG. 2C, the charge carriers generated by an X-ray photon incident around the footprint of one of these discrete portions of the electric contact 119B are not substantially shared with surrounding guard rings. The area around a discrete portion of the electric contact 119B in which substantially all (more than 95%, more than 98% or more than 99% of) charge carriers generated by an X-ray photon incident therein flow to the discrete portion of the electric contact 119B is called a pixel associated with the discrete portion of the electric contact 119B. Namely, less than 5%, less than 2% or less than 1% of these charge carriers flow beyond the pixel associated with the one discrete portion of the electric contact 119B, when the X-ray photon hits inside the pixel. The pixels may be organized in any suitable array, such as, a square array, a triangular array and a honeycomb array. The pixels may have any suitable shape, such as, circular, triangular, square, rectangular, and hexangular. The pixels may be individually addressable, and the pixel array may be encompassed by one or several guard rings (such as guard rings 211 and 212). The guard ring 212 may have discrete segments.

Figure 3B:
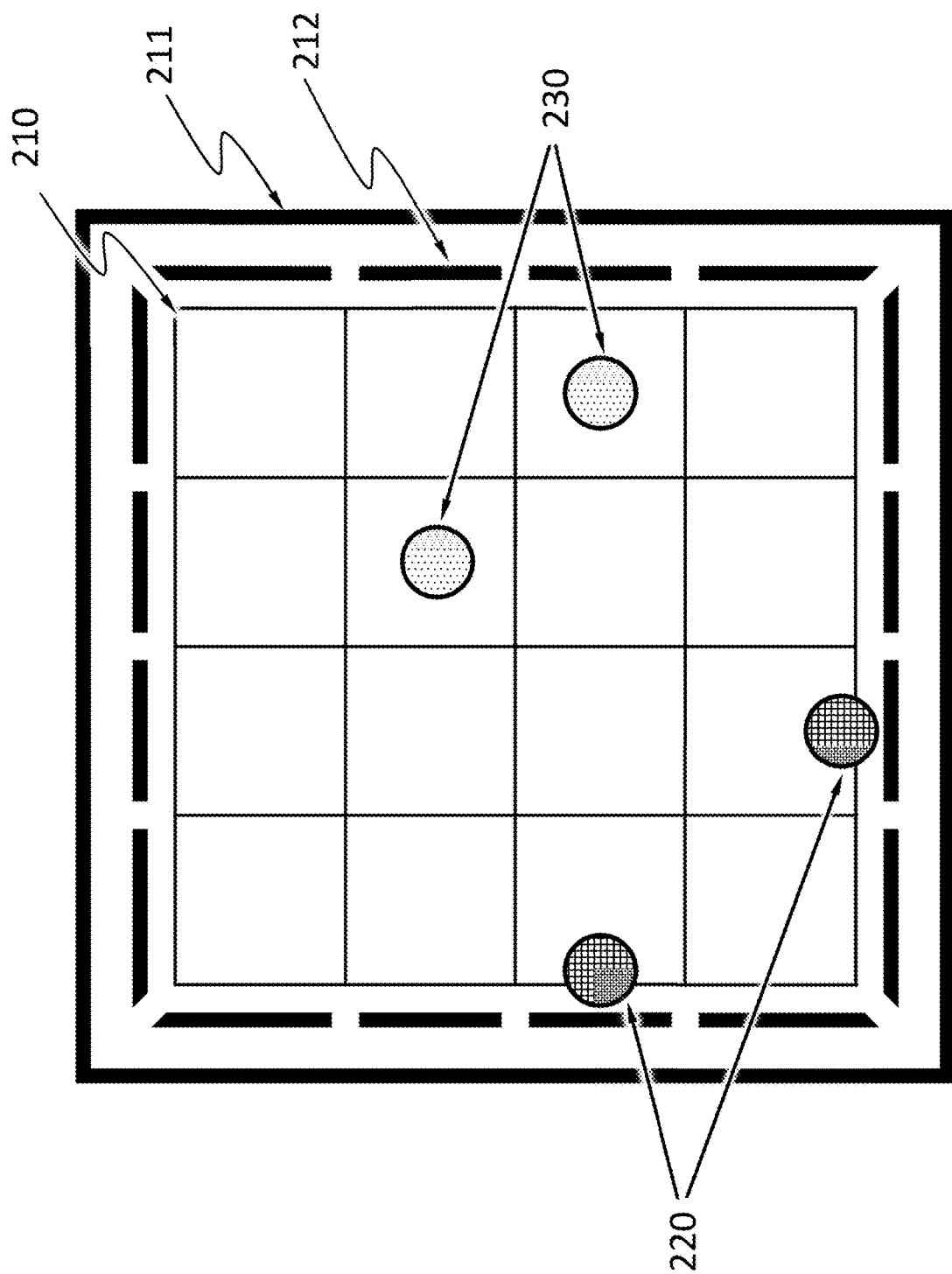
FIG. 3B schematically shows an array of pixels in the detector, according to an embodiment.

FIG. 3B shows an exemplary array of pixels in a semiconductor X-ray detector, according to an embodiment. When an X-ray photon hits the array, it may be absorbed and cause multiple charge carriers to be generated. The carriers may transport in various directions, e.g. drift along the direction of an electric field and diffuse in all directions. In FIG. 3B, each circle (e.g. 220, 230) represents the footprint of a transport area of charge carriers generated by a photon ("transport area" used in the present disclosure means a space the carriers generated by a photon are transported into).

As shown in FIG. 3B, a transport area may sit inside a pixel (e.g. transport areas 230), or on a boundary of a pixel and a segment of the guard ring (e.g. transport areas 220).

As discussed above, when a transport area sits on a boundary of a pixel and a segment of the guard ring, charge sharing occurs, which may cause issues for energy measurement. Charge sharing may also lead to errors in counting the number photons. In an embodiment, the electronic system including 121 and 122 in an X-ray detector can still accurately measure the energy of an X-ray photon even if a charge sharing occurs to the carriers generated by the X-ray photon.

A size of a pixel can be determined by design, based on fabrication process. As shown in FIG. 3B, the size of each pixel is designed to be the same and enough to cover a transport area when the corresponding photon hits around the center of the pixel. If the size of a pixel is too small, e.g. smaller than a transport area, then charge sharing can happen all the time. On the other hand, if the size of a pixel is too large, it is very likely for multiple photons to hit the pixel at the same time, which can generate difficulty for accurate X-ray detection and image generation.

Figure 4:
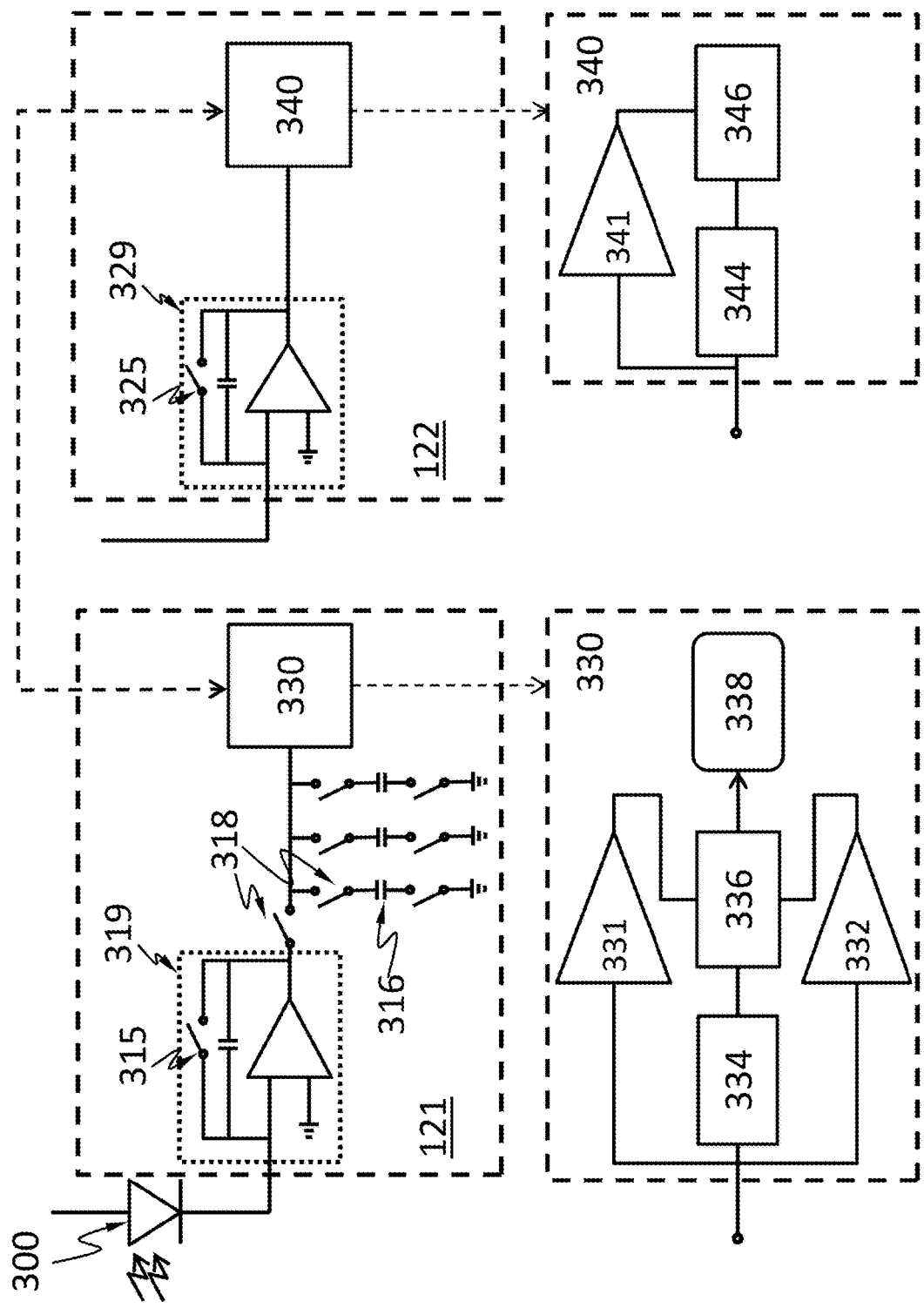
FIG. 4 schematically shows component diagrams of electronic systems of a pixel and a segment of the guard ring of the detector, according to an embodiment.

FIG. 4 shows component diagrams of two electronic systems of a semiconductor X-ray detector—electronic system 121 for pixels and electronic system 122 for segments of the guard ring, according to an embodiment. In this example, as shown in FIG. 4, the electronic system 121 is configured to process signals from an electrode of a diode 300 in a pixel; and the electronic system 122 configured to process signals from a segment of the guard ring.

Figure 5A:
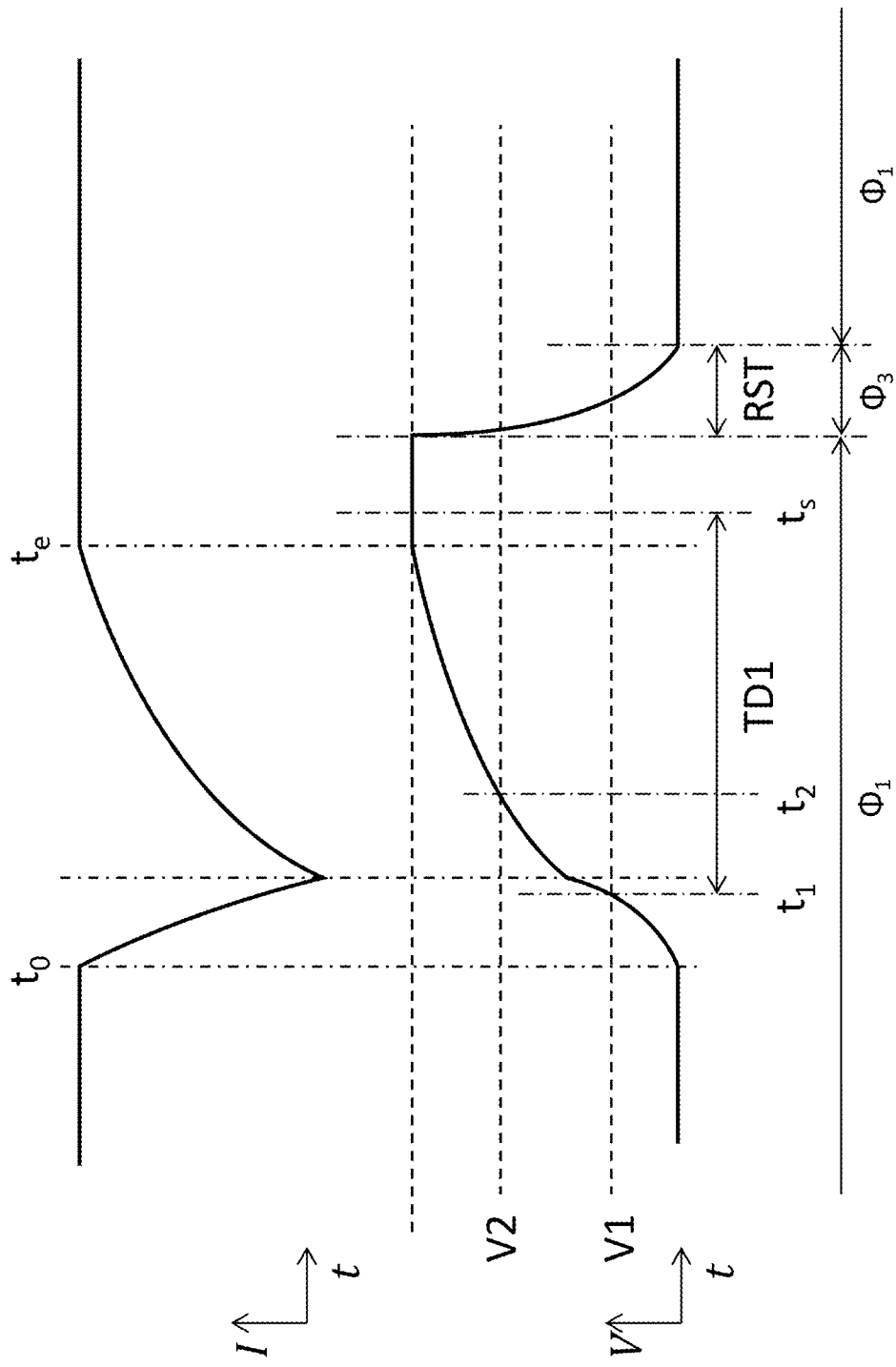
FIG. 5A schematically shows a temporal change of the electric current flowing through an electrode (upper curve) of a diode or an electric contact of a resistor of an X-ray absorption layer exposed to X-ray, the electric current caused by charge carriers generated by an X-ray photon incident on the X-ray absorption layer, and a corresponding temporal change of the voltage of the electrode (lower curve), when no charge sharing occurs, according to an embodiment.

In this example, the electronic system 121 may include a capacitor module 319, one or more sampling capacitors 316, a plurality of control switches 318, and a data processing module 330. As shown in FIG. 4, the capacitor module 319 is electrically connected to the electrode of the diode 300 or the electric contact. The capacitor module 319 is configured to collect charge carriers from the electrode. The capacitor module 319 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode may accumulate on the capacitor over a period of time ("integration period") (e.g., as shown in FIG. 5A, between $t_0$ and $t_1$, or between $t_1$ and $t_2$). After the integration period has expired, the capacitor voltage is sampled and then reset by a reset switch 315. The capacitor module 319 can include a capacitor directly connected to the electrode.

When no charge sharing occurs, the plurality of control switches 318 are closed such that each of the one or more sampling capacitors 316 is charged with the voltage from the front end (diode and amplifier).

As shown in FIG. 4, the electronic system 122 may include a capacitor module 329, and a data processing module 330. The capacitor module 329 is electrically connected to the segment. Like the capacitor module 319, the capacitor module 329 is configured to collect charge carriers from the segment. The capacitor module 329 can include a capacitor in the feedback path of a CTIA. Charge carriers from the electrode may accumulate on the capacitor over a period of time ("integration period") (e.g., as shown in FIG. 5A, between $t_0$ and $t_1$, or between $t_1$ and $t_2$). After the integration period has expired, the capacitor is reset by a reset switch 325. The capacitor module 329 can include a capacitor directly connected to the electrode.

Electronic systems 121 and 122 in FIG. 4 may comprise data processing modules, 330 and 340 respectively, that may include downstream circuits for interpreting and processing signal from upstream of the electronic system 121 and 122.

According to an embodiment, the data processing module 330 includes a first voltage comparator 331, a second voltage comparator 332, a counter 338, a voltmeter 334 and a controller 336.

With no charge sharing, the first voltage comparator 331 is configured to compare a voltage (e.g. a voltage of an electrode or a diode 300) to a first threshold. The diode may be a diode formed by the first doped region 111, one of the discrete regions 114 of the second doped region 113, and the optional intrinsic region 112. Alternatively, the first voltage comparator 331 is configured to compare the voltage of an electric contact (e.g., a discrete portion of electric contact 119B) to a first threshold. The first voltage comparator 331 may be configured to monitor the voltage directly, or calculate the voltage by integrating an electric current flowing through the diode or electric contact over a period of time. The first voltage comparator 331 may be controllably activated or deactivated by the controller 336. The first voltage comparator 331 may be a continuous comparator. Namely, the first voltage comparator 331 may be configured to be activated continuously, and monitor the voltage continuously. The first voltage comparator 331 configured as a continuous comparator reduces the chance that the system 121 misses signals generated by an incident X-ray photon. The first voltage comparator 331 configured as a continuous comparator is especially suitable when the incident X-ray intensity is relatively high. The first voltage comparator 331 may be a clocked comparator, which has the benefit of lower power consumption. The first voltage comparator 331 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 331 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 332 is configured to compare a voltage (e.g. a voltage of an electrode or a diode 300) to a second threshold. The second voltage comparator 332 may be configured to monitor the voltage directly, or calculate the voltage by integrating an electric current flowing through the diode or the electric contact over a period of time. The second voltage comparator 332 may be a continuous comparator. The second voltage comparator 332 may be controllably activate or deactivated by the controller 336. When the second voltage comparator 332 is deactivated, the power consumption of the second voltage comparator 332 may be less than 1%, less than 5%, less than 10% or less than 20% of the power consumption when the second voltage comparator 332 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 332 and the first voltage comparator 331 may be the same component. Namely, the system 121 may have one voltage comparator that can compare a voltage with two different thresholds at different times.

The first voltage comparator 331 or the second voltage comparator 332 may include one or more op-amps or any other suitable circuitry. The first voltage comparator 331 or the second voltage comparator 332 may have a high speed to allow the system 121 to operate under a high flux of incident X-ray.

The counter 338 is configured to register a number of X-ray photons reaching a corresponding diode or resistor. The counter 338 may be a software component (e.g., a number stored in a computer memory) or a hardware component (e.g., a 4017 IC and a 7490 IC).

The controller 336 may be a hardware component such as a microcontroller and a microprocessor. The controller 336 may be configured to start a time delay from a time at which the first voltage comparator 331 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electric contact is used. The controller 336 may be configured to keep deactivated the second voltage comparator 332, the counter 338 and any other circuits the operation of the first voltage comparator 331 does not require, before the time at which the first voltage comparator 331 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 336 may be configured to activate the second voltage comparator during (including the beginning and the expiration) the time delay. In an embodiment, the controller 336 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 336 itself may be deactivated until the output of the first voltage comparator 331 activates the controller 336 when the absolute value of the voltage equals or exceeds the absolute value of the first threshold.

The controller 336 may be configured to cause the number registered by the counter 338 to increase by one, if, during the time delay, the second voltage comparator 332 determines that the absolute value of the voltage equals or exceeds the absolute value of the second threshold.

The controller 336 may be configured to cause the voltmeter 334 to measure the voltage upon expiration of the time delay. The controller 336 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 336 may connect the electrode to the electrical ground by controlling the reset switch 315 or 325. The switch may be a transistor such as a field-effect transistor (FET).

In an embodiment, the system 121 has no analog filter network (e.g., a RC network). In an embodiment, the system 121 has no analog circuitry.

According to an embodiment, the data processing module 340 includes a voltage comparator 341, a voltmeter 344 and a controller 346.

The voltage comparator 341 is configured to monitor the voltage of an electric contact (e.g., a segment of the guard ring 115). The voltage comparator 341 may be configured to monitor the voltage directly, or calculate the voltage by integrating an electric current flowing through the electric contact over a period of time. The voltage comparator 341 may be controllably activated or deactivated by the controller 346. The first voltage comparator 341 may be a continuous comparator. Namely, the voltage comparator 341 may be configured to be activated continuously, and monitor the voltage continuously. The voltage comparator 341 may also be a clocked comparator.

When no charge sharing occurs, the two electronic systems 121 and 122 may operate independently and process signals generated from their respective corresponding sources (a pixel or a segment of the guard ring). When no charge sharing occurs on the pixel corresponding to the electronic system 121, the plurality of control switches 318 are closed such that the voltage from the front end (diode and amplifier) is reflected on the sampling capacitors and measured by the data processing module 330. The same voltage may also be compared with a threshold by the data processing module 330 (e.g., using the first voltage comparator 331 and/or the second voltage comparator 332).

When no charge sharing occurs, after the rate of change of the voltage becomes substantially zero, the voltage is proportional to the amount of charge carriers generated by an X-ray photon, which relates to the energy of the X-ray photon. However, when charge sharing occurs between the pixel corresponding to the electronic system 121 and a segment of the guard ring, the voltage measured by the electronic system 121 in FIG. 4 is not enough to estimate the accurate amount of charge carriers generated by the X-ray photon.

In one example, a single X-ray photon may hit on a common boundary of at least one pixel and one segment of the guard ring, or on an area between the two, and thus cause charge carriers generated and transported into the pixel and the segment at the same time. In this case, both electronic systems 121 and 122 may sense a voltage increase caused by a portion of the charge carriers.

In this example, the two electronic systems 121 and 122 operate in different phases: phase 1 ($\Phi_1$), and phase 3 ($\Phi_3$). The pixel and the segment may be in phase 1 when they are ready to detect photons. The two electronic systems 121 and 122 may cooperate either by communicating directly to each other or by a central controller controlling all pixels and all segments of the guard ring of the X-ray detector. Based on their cooperation, the two systems 121 and 122 can determine that charge sharing occurs on the pixels and the segment(s), e.g. when they see voltage changes by charge carriers at the same time or in a same time period.

The controller 336, in an embodiment, may be configured to disregard one X-ray photon, then the counter 338 may not be increased, after the charge sharing is detected.

In an embodiment, after the charge sharing is detected and the rate of change of the voltage is substantially zero, the controllers 336 and 346 may be configured to connect the electrode to an electrical ground, so as to reset the voltage and discharge any charge carriers accumulated on the electrodes, thus enter phase 3. The electrode is connected to an electrical ground after the expiration of the time delay, for a finite reset time period. During phase 3, the controller 336 and 346 may connect the electrode to the electrical ground by controlling the reset switch 315 and 325. The switch may be a transistor such as a field-effect transistor (FET).

After phase 3, the pixel and the segment of the guard ring may enter phase 1 again, such that they are ready to measure next incident photon.

FIG. 5A schematically shows a temporal change of the electric current flowing through an electrode (upper curve) of a diode or an electric contact of a resistor of an X-ray absorption layer exposed to X-ray, the electric current caused by charge carriers generated by an X-ray photon incident on the X-ray absorption layer, and a corresponding temporal change of the voltage of the electrode (lower curve), when no charge sharing occurs, according to an embodiment. The electrode is the diode 300 as shown in FIG. 4, when no charge sharing occurs on the pixel and the segment of the guard ring.

The voltage of the electrode may be an integral of the electric current with respect to time. As discussed above, a pixel is in phase 1 when it is ready to detect an X-ray photon. During phase 1, at time to, the X-ray photon hits the diode or the resistor, charge carriers start being generated in the diode or the resistor, electric current starts to flow through the electrode of the diode or the resistor, and the absolute value of the voltage of the electrode or electric contact starts to increase. At time $t_1$, the first voltage comparator 331 determines that the absolute value of the voltage equals or exceeds the absolute value of the first threshold V1, and the controller 336 starts the time delay TD1 and the controller 336 may deactivate the first voltage comparator 331 at the beginning of TD1. If the controller 336 is deactivated before $t_1$, the controller 336 is activated at $t_1$. During TD1, the controller 336 activates the second voltage comparator 332. The term "during" a time delay as used here means the beginning and the expiration (i.e., the end) and any time in between. For example, the controller 336 may activate the second voltage comparator 332 at the expiration of TD1. If during TD1, the second voltage comparator 332 determines that the absolute value of the voltage equals or exceeds the absolute value of the second threshold V2 at time $t_2$, the controller 336 causes the number registered by the counter 338 to increase by one. At time $t_2$, all charge carriers generated by the X-ray photon drift out of the X-ray absorption layer 110. At time $t_s$, the time delay TD1 expires. In the example of FIG. 5A, time $t_s$ is after time $t_e$; namely TD1 expires after all charge carriers generated by the X-ray photon drift out of the X-ray absorption layer 110. The rate of change of the voltage is thus substantially zero at $t_s$. The controller 336 may be configured to deactivate the second voltage comparator 332 at expiration of TD1 or at $t_2$, or any time in between.

The controller 336 may be configured to cause the voltmeter 334 to measure the voltage upon expiration of the time delay TD1. In an embodiment, the controller 336 causes the voltmeter 334 to measure the voltage after the rate of change of the voltage becomes substantially zero after the expiration of the time delay TD1. When no charge sharing occurs, the voltage at this moment is proportional to the amount of charge carriers generated by an X-ray photon, which relates to the energy of the X-ray photon. The controller 336 may be configured to determine the energy of the X-ray photon based on voltage the voltmeter 334 measures. One way to determine the energy is by binning the voltage. The counter 338 may have a sub-counter for each bin. When the controller 336 determines that the energy of the X-ray photon falls in a bin, the controller 336 may cause the number registered in the sub-counter for that bin to increase by one. Therefore, the system 121 may be able to detect an X-ray image and may be able to resolve X-ray photon energies of each X-ray photon.

After TD1 expires, the controller 336 connects the electrode to an electric ground for a reset period RST to allow charge carriers accumulated on the electrode to flow to the ground and reset the voltage. After the expiration of TD1 and before the reset period RST, the pixel may end phase 1 and enter phase 3.

After RST, the system 121 enters phase 1 again and is ready to detect another incident X-ray photon. Implicitly, the rate of incident X-ray photons the system 121 can handle in the example of FIG. 5A is limited by 1/(TD1+RST). If the first voltage comparator 331 has been deactivated, the controller 336 can activate it at any time before RST expires. If the controller 336 has been deactivated, it may be activated before RST expires.

Figure 5B:
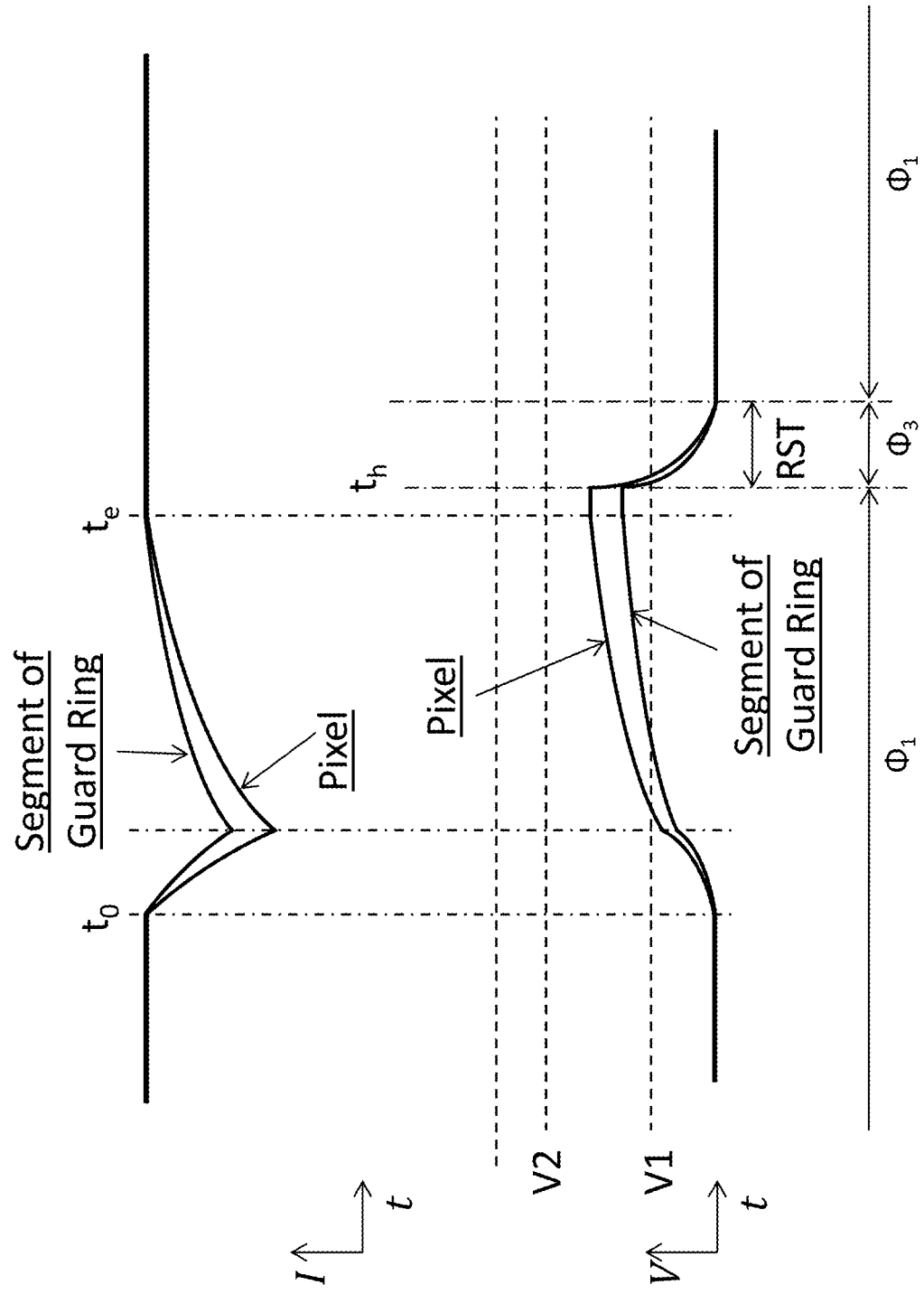
FIG. 5B schematically shows temporal changes of the electric currents (upper curve) flowing through an electrode of a pixel and a segment of a guard ring, the electric currents caused by charge carriers generated by an X-ray photon incident on the X-ray absorption layer, and corresponding temporal changes of the voltages of the electrode and the segment (lower curves), when charge sharing occurs between the pixel and the segment.

FIG. 5B schematically shows temporal changes of the electric currents flowing through two electrodes, one from a pixel and one from a segment of the guard ring (upper curves) of the X-ray absorption layer exposed to X-ray, the electric currents caused by charge carriers generated by an X-ray photon incident on the X-ray absorption layer, and corresponding temporal changes of the voltages of electric contact of the pixel and the segment (lower curves), when charge sharing occurs, according to an embodiment.

The voltage of each electrode may be an integral of the corresponding electric current with respect to time. As discussed above, the pixel and the segment of the guard ring are in phase 1 when they are ready to detect an X-ray photon. During phase 1, at time to, the X-ray photon hits at an area near a boundary between the pixel and the segment of the guard ring, charge carriers start being generated, electric current starts to flow through the electric contact of the pixel and the segment, and the absolute value of each of voltages on the electric contact and the segment starts to increase. Then, the charge sharing between a pixel and a segment occurs.

According to an embodiment, the absolute values of the two voltages start to increase at two different times, e.g. $t_{01}$ and $t_{02}$, that are within a same time period. For example, the same time period may be 10 µs, 1 µs, 100 ns, or 10 ns. If so, the two pixels determine that charge sharing occurs at the pixel and the segment of the guard ring.

As shown in FIG. 5B, the pixel and the segment of the guard ring may have different increasing rates of the voltages and/or currents, because the amount of transporting charge carriers may be different.

Phase 1 may end at or after the stabilization of the voltages at the pixel and the segment of the guard ring. In the example of FIG. 5B, at time $t_e$, all charge carriers generated by the X-ray photon drift out of the X-ray absorption layer 110. As such, the rate of change of the voltage at each pixel may be substantially zero after $t_e$. Here, at time $t^h$ after $t_e$, phase 1 ends.

After the voltage is stable, the pixel and the segment of the guard ring may enter phase 3. During phase 3, the controllers 336 and 346 connect the electrodes to the electric ground for a reset period RST to allow charge carriers accumulated on the electrode to flow to the ground and reset the voltage.

After RST, each of system 121 and 122 enters phase 1 again, the pixel and the segment are ready to detect another incident X-ray photon. If the voltage comparator 331 or 341 has been deactivated, the controller 336 or 346 can activate it at any time before RST expires. If the controller 336 or 346 has been deactivated, it may be activated before RST expires.

Figure 6:
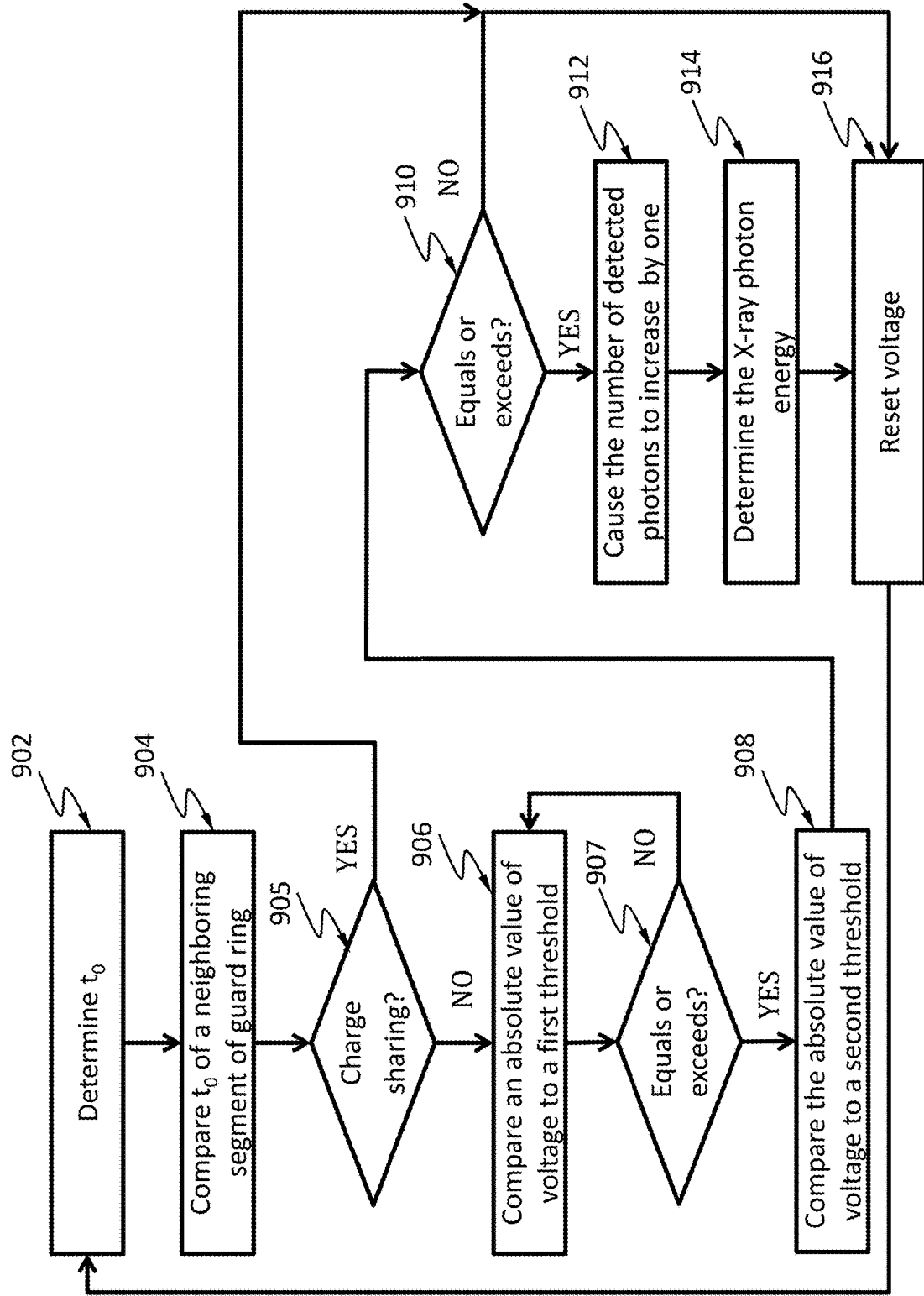
FIG. 6 shows a flow chart for a method suitable for detecting X-ray based on a system that can detect charge sharing between a pixel and a segment of the guard ring in FIG. 4, according to an embodiment.

FIG. 6 shows a flow chart for a method suitable for detecting X-ray based on a system that can detect charge sharing between a pixel and a segment of the guard ring in FIG. 4, according to an embodiment. At 902, determine a time to at which a voltage of an electrode starts to increase. The electrode may be a diode or an electric contact of a resistor of a pixel exposed to X-ray. At 904, compare the time to with that of at least one segment of the guard ring. At 905, it is determined whether charge sharing occurs, e.g. by detecting whether the time $t_0$ of the Pixel 1 and the time to of a segment of the guard ring are within a same time period, e.g. 10 µs, 1 µs, 100 ns, or 10 ns. If charge sharing occurs, the process moves to 916. Otherwise, if charge sharing does not occur, the process moves to 906.

At 906, compare, e.g., using the first voltage comparator 331, an absolute value of the voltage of an electrode of a diode or an electric contact of a resistor exposed to X-ray, to a first threshold V1. At 907, if the absolute value of the voltage does not equal or exceed the absolute value of the first threshold, the process goes back to step 906. If the absolute value of the voltage equals or exceeds the absolute value of the first threshold at 907, the process continues to step 908, e.g. after a time delay or after the voltage is stabilized. At 908, compare, e.g., using the second voltage comparator 332, the absolute value of the voltage to a second threshold. Then, the process moves to 910.

At 910, if the absolute value of the voltage does not equal or exceed the absolute value of the second threshold, the process goes to step 916. If the absolute value of the voltage or the sum voltage equals or exceeds the absolute value of the second threshold, the process continues to step 912. At 912, cause, e.g., using the controller 336, the number registered in the counter 338 to increase by one. At 914, determine, e.g., using the controller 336, the X-ray photon energy based on the voltage. There may be a counter for each of the energy bins. After measuring the X-ray photon energy, the counter for the bin to which the photon energy belongs can be increased by one. The method goes to step 916 after step 914. At 916, reset the voltage to an electrical ground, e.g., by connecting the electrode of the diode or an electric contact of a resistor to an electrical ground. After 916, the process may go back to 902.

Figure 7:
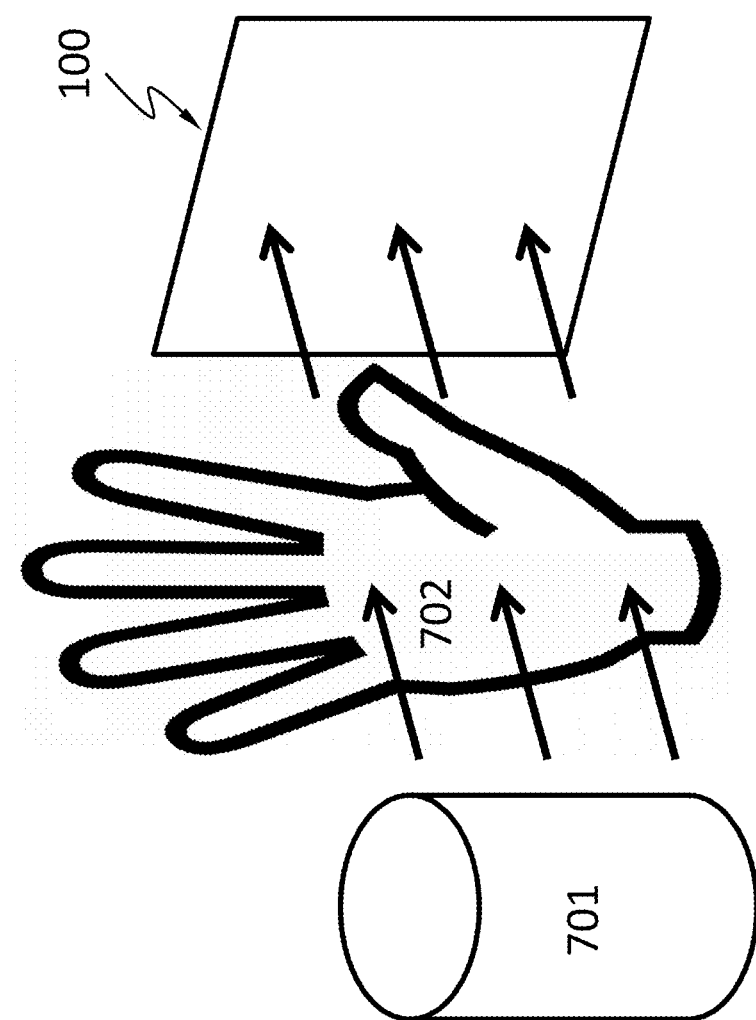
FIG. 7 schematically shows a system comprising the detector described herein, suitable for medical imaging such as chest X-ray radiography, abdominal X-ray radiography, etc., according to an embodiment.

FIG. 7 schematically shows a system comprising the semiconductor X-ray detector 100 described herein. The system may be used for medical imaging such as chest X-ray radiography, abdominal X-ray radiography, dental X-ray radiography, etc. The system comprises an X-ray source 701. X-ray emitted from the X-ray source 701 penetrates an object 702 (e.g., a human body part such as chest, limb, abdomen, mouth), is attenuated by different degrees by the internal structures of the object 702 (e.g., bones, muscle, fat, organs and teeth, etc.), and is projected to the semiconductor X-ray detector 100. The semiconductor X-ray detector 100 forms an image by detecting the intensity distribution of the X-ray.

Figure 8:
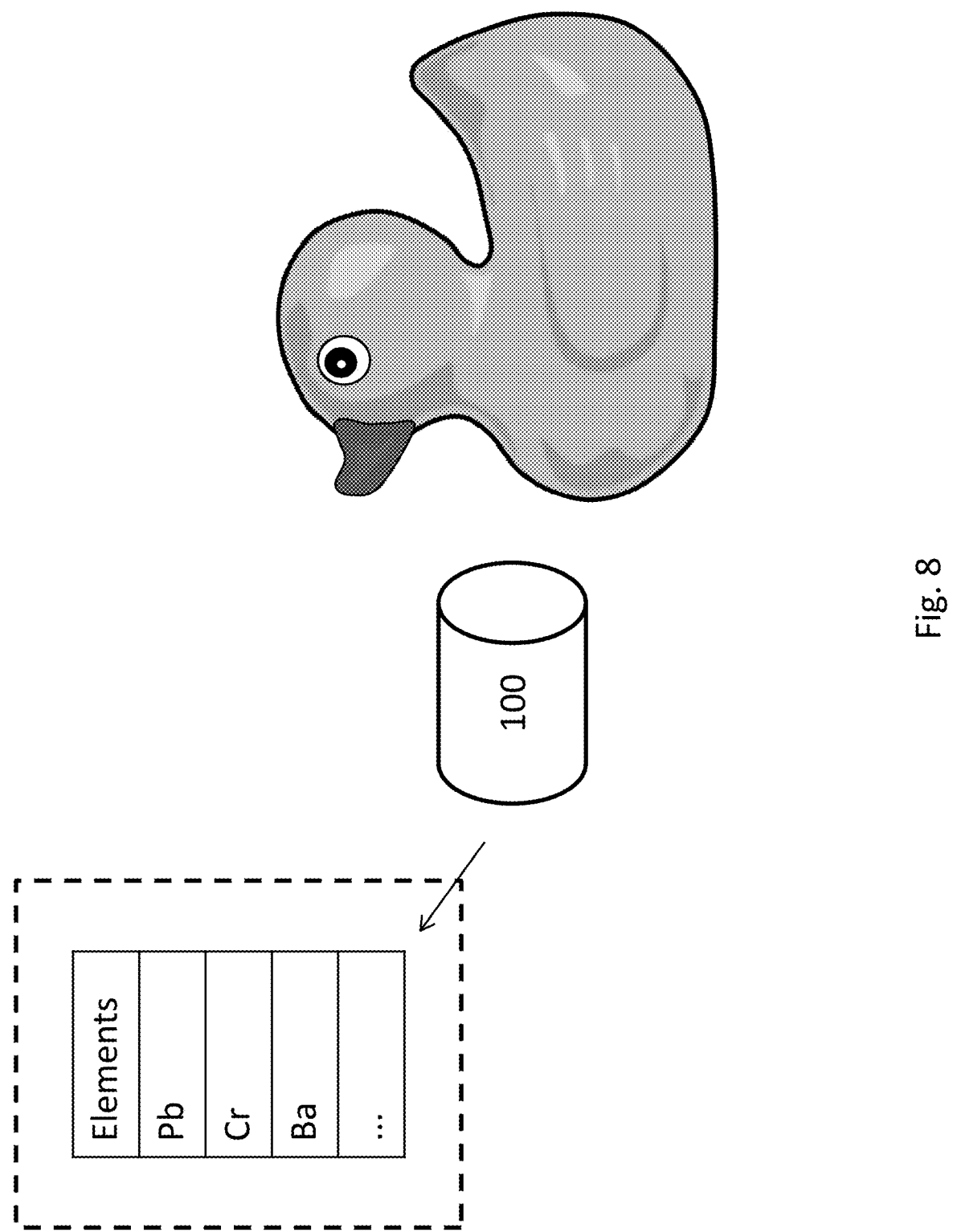
FIG. 8 schematically shows an element analyzer, according to an embodiment.

FIG. 8 schematically shows an element analyzer comprising the semiconductor X-ray detector 100 described herein. The element analyzer measurer is capable of detecting presence of one or more elements of interest on an object such as a toy. A high-energy beam of charged particles such as electrons or protons, or a beam of X-rays, is directed onto the object. Atoms of the objects are excited and emit X-ray at specific wavelengths that are characteristic of the elements. The X-ray detector 100 receives the emitted X-ray and determines the presence of the elements based on the energy of the emitted X-ray. For example, the X-ray detector 100 may be configured to detect X-ray at wavelengths Pb would emit. If the X-ray detector 100 actually receives X-ray from the object at these wavelengths, it can tell that Pb is present. The semiconductor X-ray detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this semiconductor X-ray detector 100 in place of a photographic plate, a photographic film, a PSP plate, an X-ray image intensifier, a scintillator, or another semiconductor X-ray detector.

Figure 9:
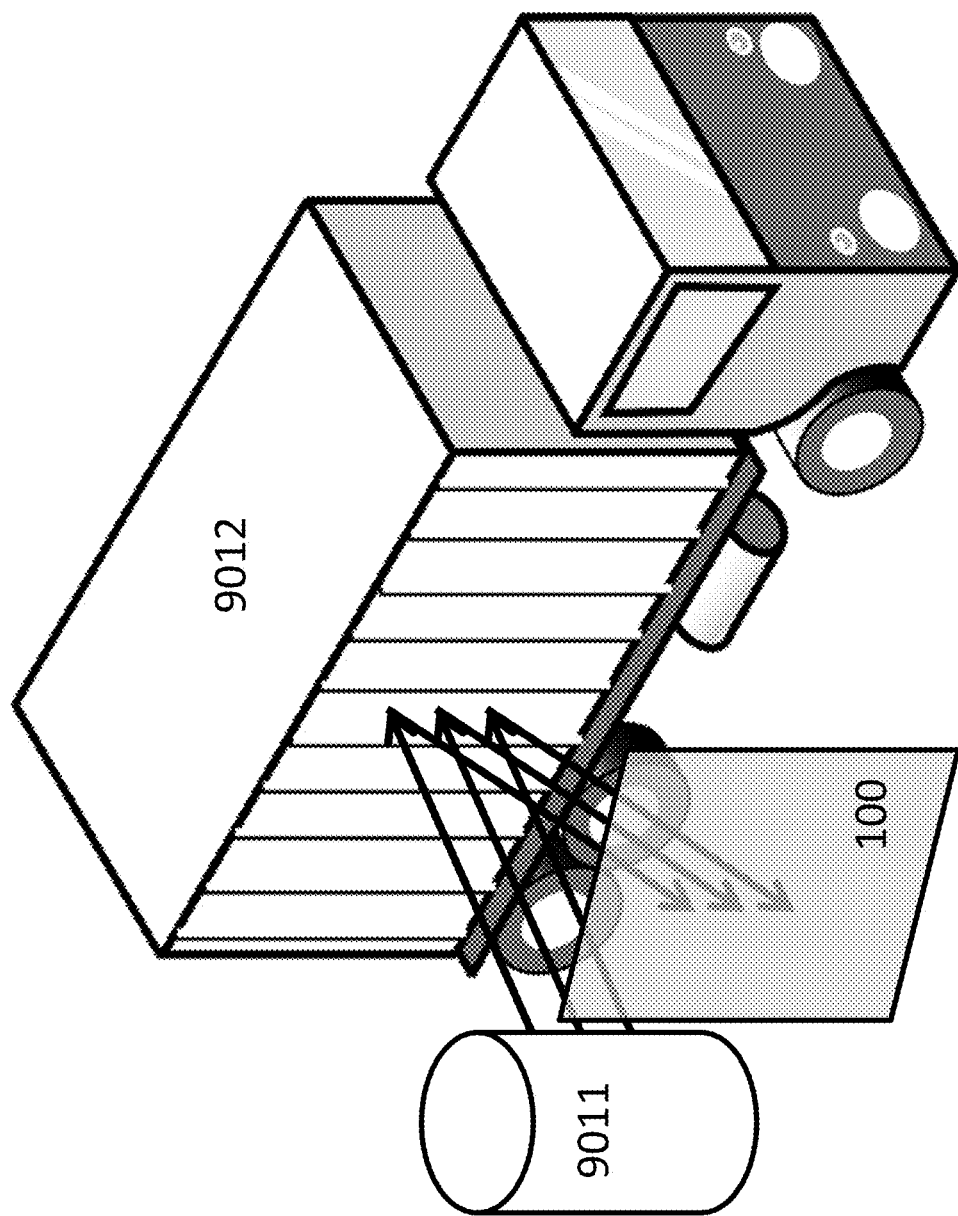
FIG. 9 schematically shows a cargo scanning or non-intrusive inspection (NII) system comprising the detector described herein, according to an embodiment.

FIG. 9 schematically shows a cargo scanning or non-intrusive inspection (NII) system comprising the semiconductor X-ray detector 100 described herein. The system may be used for inspecting and identifying goods in transportation systems such as shipping containers, vehicles, ships, luggage, etc. The system comprises an X-ray source 9011. X-ray emitted from the X-ray source 9011 may backscatter from an object 9012 (e.g., shipping containers, vehicles, ships, etc.) and be projected to the semiconductor X-ray detector 100. Different internal structures of the object 9012 may backscatter X-ray differently. The semiconductor X-ray detector 100 forms an image by detecting the intensity distribution of the backscattered X-ray and/or energies of the backscattered X-ray photons.

Figure 10:
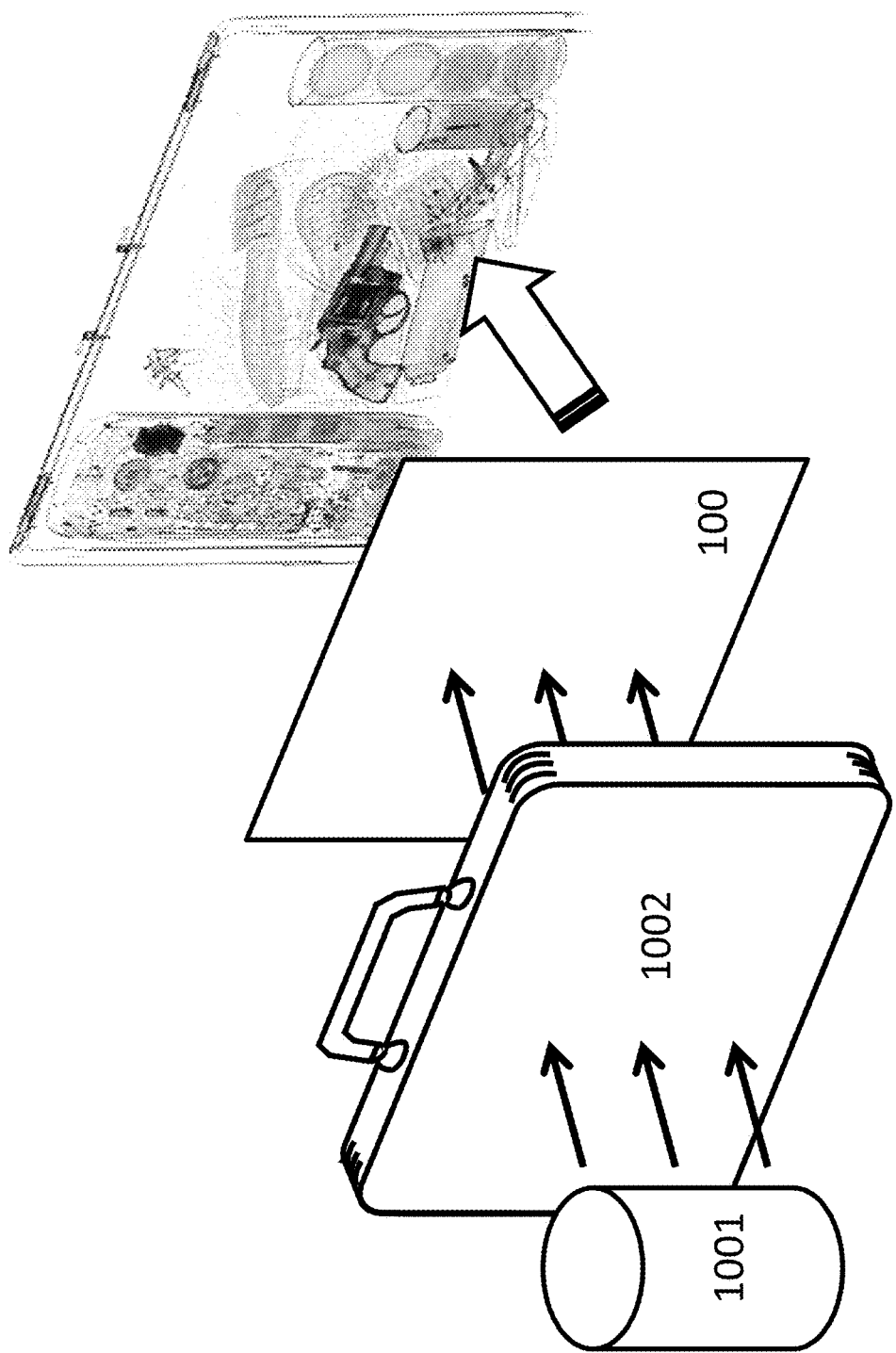
FIG. 10 schematically shows another cargo scanning or non-intrusive inspection (NII) system comprising the detector described herein, according to an embodiment.

FIG. 10 schematically shows another cargo scanning or non-intrusive inspection (NII) system comprising the semiconductor X-ray detector 100 described herein. The system may be used for luggage screening at public transportation stations and airports. The system comprises an X-ray source 1001. X-ray emitted from the X-ray source 1001 may penetrate a piece of luggage 1002, be differently attenuated by the contents of the luggage, and projected to the semiconductor X-ray detector 100. The semiconductor X-ray detector 100 forms an image by detecting the intensity distribution of the transmitted X-ray. The system may reveal contents of luggage and identify items forbidden on public transportation, such as firearms, narcotics, edged weapons, flammables.

Figure 11:
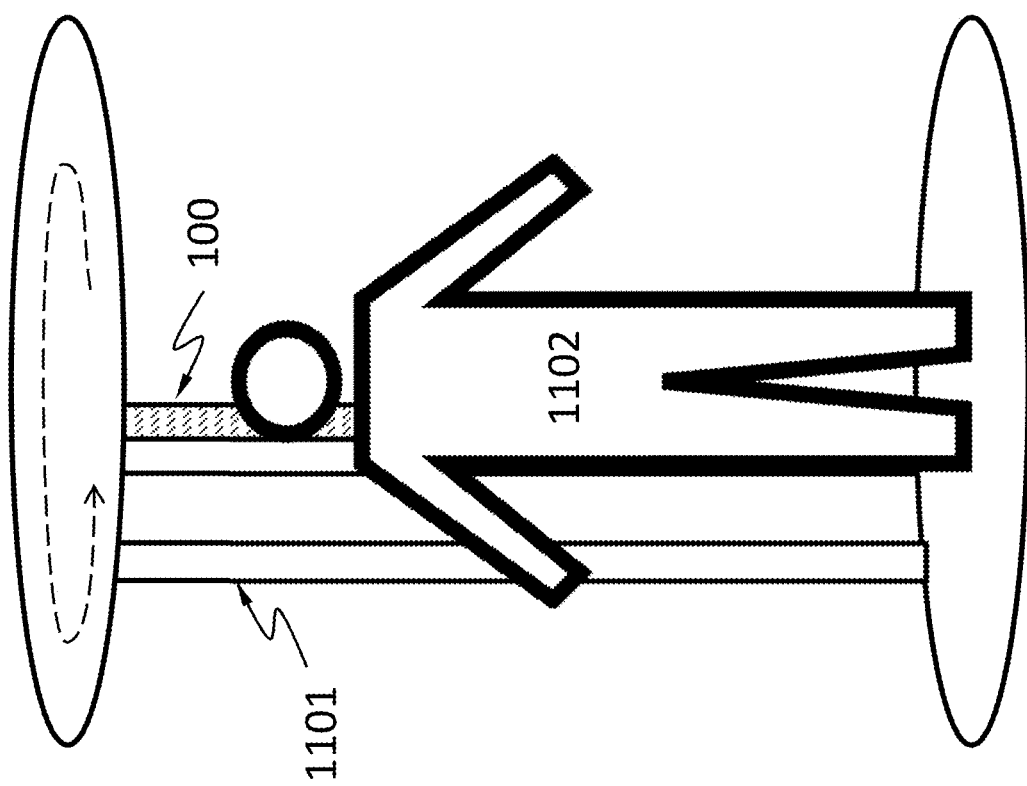
FIG. 11 schematically shows a full-body scanner system comprising the detector described herein, according to an embodiment.

FIG. 11 schematically shows a full-body scanner system comprising the semiconductor X-ray detector 100 described herein. The full-body scanner system may detect objects on a person's body for security screening purposes, without physically removing clothes or making physical contact. The full-body scanner system may be able to detect non-metal objects. The full-body scanner system comprises an X-ray source 1101. X-ray emitted from the X-ray source 1101 may backscatter from a human 1102 being screened and objects thereon, and be projected to the semiconductor X-ray detector 100. The objects and the human body may backscatter X-ray differently. The semiconductor X-ray detector 100 forms an image by detecting the intensity distribution of the backscattered X-ray. The semiconductor X-ray detector 100 and the X-ray source 1101 may be configured to scan the human in a linear or rotational direction.

Figure 12:
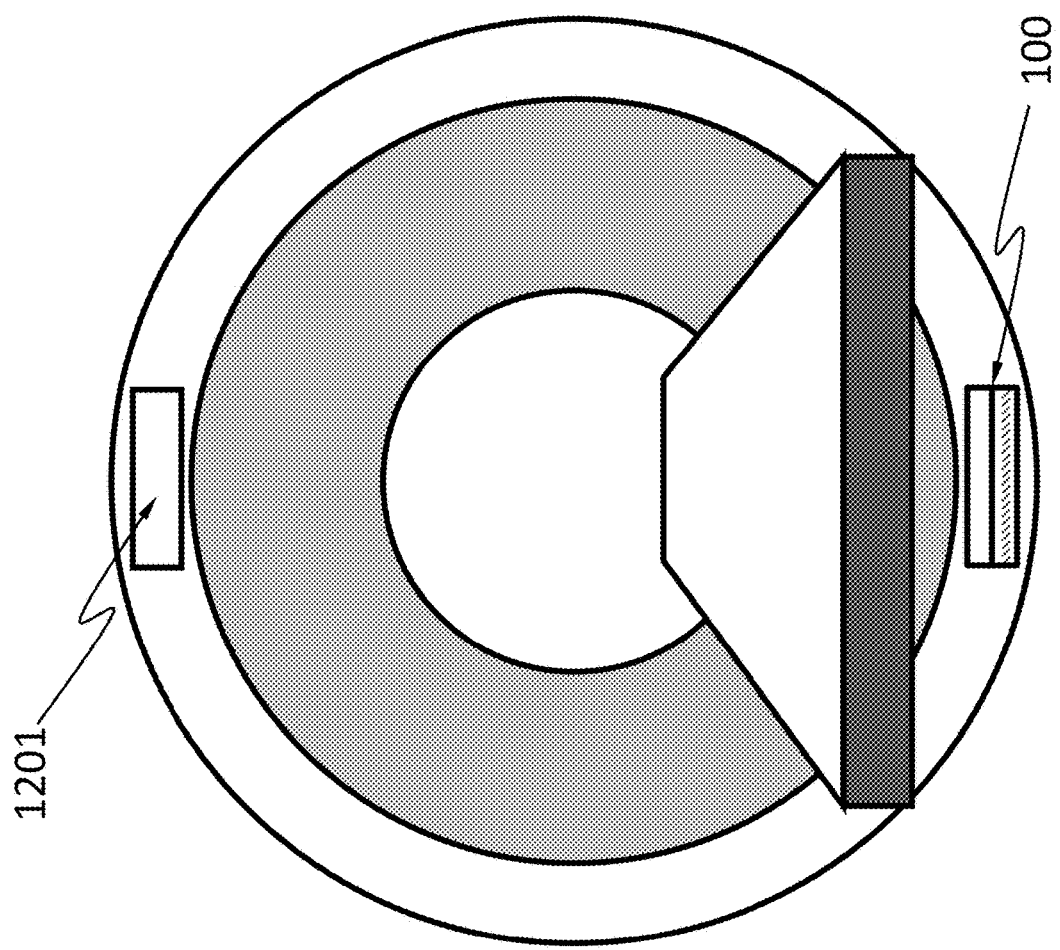
FIG. 12 schematically shows an X-ray computed tomography (X-ray CT) system comprising the detector described herein, according to an embodiment FIG. 13 schematically shows an electron microscope comprising the detector described herein, according to an embodiment.

FIG. 12 schematically shows an X-ray computed tomography (X-ray CT) system comprising the semiconductor X-ray detector 100 described herein. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the semiconductor X-ray detector 100 described herein and an X-ray source 1201. The semiconductor X-ray detector 100 and the X-ray source 1201 may be configured to rotate synchronously along one or more circular or spiral paths.

Figure 13:
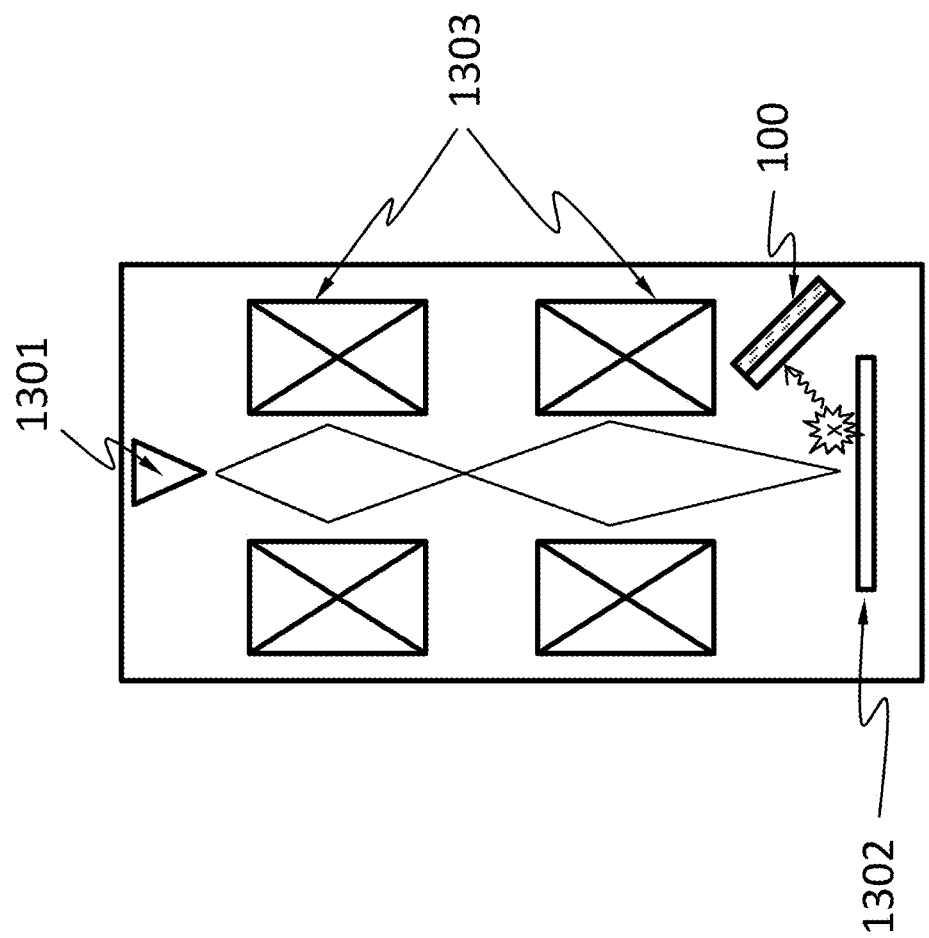

FIG. 13 schematically shows an electron microscope comprising the semiconductor X-ray detector 100 described herein. The electron microscope comprises an electron source 1301 (also called an electron gun) that is configured to emit electrons. The electron source 1301 may have various emission mechanisms such as thermionic, photo-cathode, cold emission, or plasmas source. The emitted electrons pass through an electronic optical system 1303, which may be configured to shape, accelerate, or focus the electrons. The electrons then reach a sample 1302 and an image detector may form an image therefrom. The electron microscope may comprise the semiconductor X-ray detector 100 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the semiconductor X-ray detector 100.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A detector, comprising:
   a plurality of pixels;
   a first guard ring comprising a plurality of segments, wherein the detector is configured to detect charge carriers collected by the segments;
   a controller configured to detect charge sharing between at least one pixel of the plurality of pixels and at least one segment of the first guard ring.

2. The detector of claim 1, wherein the plurality of pixels are arranged in an array.

3. The detector of claim 1, wherein the detector is configured to count numbers of X-ray photons that incident on each pixel of the plurality of pixels and whose energies fall in a plurality of bins, within a period of time, based on charge carriers generated by the X-ray photons and collected by the each pixel.

4. The detector of claim 1, wherein the first guard ring encompasses the plurality of pixels.

5. The detector of claim 1, wherein the controller is configured to detect charge sharing by determining that a voltage detected from the at least one pixel and a voltage detected from the segment start to change in a same time period.

6. The detector of claim 1, wherein the controller is configured to disregard one photon of the X-ray photons when the controller detects charge sharing between the at least one pixel and the at least one segment.

7. The detector of claim 1, further comprising a second guard ring encompasses the first guard ring.

8. A system, comprising the detector of claim 1, and an X-ray source, wherein the system is configured for performing X-ray radiography on human body, limb, teeth.

9. A system comprising the detector of claim 1, and an X-ray source, wherein the system is configured to detect X-ray fluorescence (XRF).

10. A system comprising the detector of claim 1, wherein the system is an X-ray telescope, or an X-ray microscopy, wherein the system is configured to perform mammography, industrial defect detection, microradiography, casting inspection, weld inspection, or digital subtraction angiography.

11. A cargo scanning or non-intrusive inspection (NII) system, comprising the apparatus of claim 1 and an X-ray source, wherein the cargo scanning or non-intrusive inspection (NII) system is configured for forming an image based on backscattered X-ray.

12. A cargo scanning or non-intrusive inspection (NII) system, comprising the apparatus of claim 1 and an X-ray source, wherein the cargo scanning or non-intrusive inspection (NII) system is configured for forming an image based on X-ray transmitted through an object inspected.

13. A full-body scanner system comprising the apparatus of claim 1 and an X-ray source.

14. An X-ray computed tomography (X-ray CT) system comprising the apparatus of claim 1 and an X-ray source.

15. An electron microscope comprising the apparatus of claim 1, an electron source and an electronic optical system.

* * * * *